(12) United States Patent
Doshi et al.

(10) Patent No.: US 9,408,847 B2
(45) Date of Patent: Aug. 9, 2016

(54) COMBINATION THERAPY

(71) Applicants: Shivang Doshi, Cambridge, MA (US); Sunkyu Kim, Cambridge, MA (US)

(72) Inventors: Shivang Doshi, Cambridge, MA (US); Sunkyu Kim, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/646,206

(22) PCT Filed: Nov. 25, 2013

(86) PCT No.: PCT/US2013/071659
§ 371 (c)(1),
(2) Date: May 20, 2015

(87) PCT Pub. No.: WO2014/085318
PCT Pub. Date: Jun. 5, 2014

(65) Prior Publication Data
US 2015/0306104 A1    Oct. 29, 2015

Related U.S. Application Data

(60) Provisional application No. 61/730,661, filed on Nov. 28, 2012.

(51) Int. Cl.
*A61K 31/519*    (2006.01)
*A61K 31/436*    (2006.01)
*A61K 45/06*    (2006.01)

(52) U.S. Cl.
CPC ............ *A61K 31/519* (2013.01); *A61K 31/436* (2013.01); *A61K 45/06* (2013.01)

(58) Field of Classification Search
CPC .......................... A61K 31/519; A61K 31/436
USPC ............................... 514/252, 258.1; 544/280
See application file for complete search history.

(56) References Cited

FOREIGN PATENT DOCUMENTS

| WO | 2011/130232 | 10/2011 | | |
|---|---|---|---|---|
| WO | WO 2011/130232 | * | 10/2011 | |
| WO | WO 2011130232 A1 | * | 10/2011 | ........... A61K 31/436 |

OTHER PUBLICATIONS

Finn, Richard S Et al.: "PD 0332991, a selective cyclin D kinase 4/6 inhibiter, preferentially inhibits proliferation of luminal estrogen receptor-positive human breast cncer cell lines in vitro", Breast Cancer Research, Current Science, Vo. 11, No. 5, p. R77, 2009.*

Jose, Baselga Et al.: "EveroLimus +n Postmenopausal Hormone-Receptor-Positive Advanced Breast Cancer", New England Journal of Medicine, The Massachusetts Medical Society, vol. 366, No. 6, pp. 520-529, 2012.*

Finn, Richard S Et al.: "PD 0332991, a selective cyclin D kinase 4/6 inhibitor, preferentially inhibits proliferation of luminal estrogen receptor-positive human breast cncer cell lines in vitro", Breast Cancer Research, Current Science, vol. 11, No. 5, p. R77, 2009.

Jose, Baselga Et al.: "Everolimus in Postmenopausal Hormone-Receptor-Positive Advanced Breast Cancer", New England Journal of Medicine, The Massachusetts Medical Society, vol. 366, No. 6, pp. 520-529, 2012.

* cited by examiner

*Primary Examiner* — Kamal Saeed
*Assistant Examiner* — Janet L Coppins
(74) *Attorney, Agent, or Firm* — Jennifer Chapman (57) ABSTRACT

The present invention relates to a pharmaceutical combination comprising (1) a first agent which is a CDK inhibitor or a pharmaceutically acceptable salt thereof and (2) a second agent which is a mTOR inhibitor or a pharmaceutically acceptable salt thereof.

10 Claims, 5 Drawing Sheets

Compound A and Compound B combination in ER+ breast cancer cell line T-47D.

COMBINATION THERAPY

FIELD OF THE INVENTION

The present invention relates to a pharmaceutical combination comprising a CDK inhibitor and a mammalian target of rapamycin (mTOR) inhibitor for the treatment of cancer; the uses of such combinations in the treatment of cancer; and to a method of treating warm-blooded animals including humans suffering cancer comprising administering to said animal in need of such treatment an effective dose of a CDK inhibitor and a mTOR inhibitor.

BACKGROUND OF THE INVENTION

CDK Inhibitors

Tumor development is closely associated with genetic alteration and deregulation of CDKs and their regulators, suggesting that inhibitors of CDKs may be useful anti-cancer therapeutics. Indeed, early results suggest that transformed and normal cells differ in their requirement for, e.g., cyclin D/CDK4/6 and that it may be possible to develop novel antineoplastic agents devoid of the general host toxicity observed with conventional cytotoxic and cytostatic drugs.

The function of CDKs is to phosphorylate and thus activate or deactivate certain proteins, including e.g. retinoblastoma proteins, lamins, histone H1, and components of the mitotic spindle. The catalytic step mediated by CDKs involves a phospho-transfer reaction from ATP to the macromolecular enzyme substrate. Several groups of compounds (reviewed in e.g. Fischer, P. M. Curr. Opin. Drug Discovery Dev. 2001, 4, 623-634) have been found to possess anti-proliferative properties by virtue of CDK-specific ATP antagonism.

At a molecular level mediation of CDK/cyclin complex activity requires a series of stimulatory and inhibitory phosphorylation, or dephosphorylation, events. CDK phosphorylation is performed by a group of CDK activating kinases (CAKs) and/or kinases such as wee1, Myt1 and Mik1. Dephosphorylation is performed by phosphatases such as cdc25(a & c), pp2a, or KAP.

CDK/cyclin complex activity may be further regulated by two families of endogenous cellular proteinaceous inhibitors: the Kip/Cip family, or the INK family. The INK proteins specifically bind CDK4 and CDK6. p16ink4 (also known as MTS1) is a potential tumour suppressor gene that is mutated, or deleted, in a large number of primary cancers. The Kip/Cip family contains proteins such as p21Cip1, Waf1, p27Kip1 and p57kip2, where p21 is induced by p53 and is able to inactivate the CDK2/cyclin(E/A) complex. Atypically low levels of p27 expression have been observed in breast, colon and prostate cancers. Conversely over expression of cyclin E in solid tumours has been shown to correlate with poor patient prognosis. Over expression of cyclin D1 has been associated with oesophageal, breast, squamous, and non-small cell lung carcinomas.

The pivotal roles of CDKs, and their associated proteins, in co-ordinating and driving the cell cycle in proliferating cells have been outlined above. Some of the biochemical pathways in which CDKs play a key role have also been described. The development of monotherapies for the treatment of proliferative disorders, such as cancers, using therapeutics targeted generically at CDKs, or at specific CDKs, is therefore potentially highly desirable. Thus, there is a continued need to find new therapeutic agents to treat human diseases.

mTOR Inhibitors mTOR is a kinase protein predominantly found in the cytoplasm of the cell. It acts as a central regulator of many biological processes related to cell proliferation, angiogenesis, and cell metabolism. mTOR exerts its effects primarily by turning on and off the cell's translational machinery, which includes the ribosomes, and is responsible for protein synthesis. mTOR is a key intracellular point of convergence for a number of cellular signaling pathways. mTOR performs its regulatory function in response to activating or inhibitory signals transmitted through these pathways, which are located upstream from mTOR in the cell. These diverse signaling pathways are activated by a variety of growth factors (including vascular endothelial growth factors (VEGFs), platelet-derived growth factor (PDGF), epidermal growth factor (EGF), insulin-like growth factor 1 (IGF-1)), hormones (estrogen, progesterone), and the presence or absence of nutrients (glucose, amino acids) or oxygen. One or more of these signaling pathways may be abnormally activated in patients with many different types of cancer, resulting in deregulated cell proliferation, tumor angiogenesis, and abnormal cell metabolism.

In spite of numerous treatment options for cancer patients, there remains a need for effective and safe therapeutic agents and a need for their preferential use in combination therapy.

SUMMARY OF THE INVENTION

The present invention relates to a pharmaceutical combination comprising (1) a first agent which is a CDK inhibitor or a pharmaceutically acceptable salt thereof and (2) a second agent that inhibits mTOR, or a pharmaceutically acceptable salt thereof. More specifically, it relates to the treatment of solid tumors and hematological malignancies using the combination. This invention also relates to the use of the combination thereof, in the management of hyperproliferative diseases like cancer, e.g., ER+ breast cancer, rhabdoid tumor.

Such combination may be for simultaneous, separate or sequential use for the treatment of a cancer.

In one embodiment, the CDK inhibitor is CDK4/6 inhibitor.

The CDK4/6 inhibitor can be, for example,

Compound A, described by Formula A below:

(A)

or pharmaceutically acceptable salt(s) thereof.

In another embodiment, the mTOR inhibitor is everolimus (hereinafter referred as Compound B) which has the chemical name ((1R,9S,12S,15R,16E,18R,19R,21R,23S,24E,26E, 28E,30S,32S,35R)-1,18-dihydroxy-12-{(1R)-2-[(1S,3R, 4R)-4-(2-hydroxyethoxy)-3-methoxycyclohexyl]-1-methylethyl}-19,30-dimethoxy-15,17,21,23,29,35-hexamethyl-11,36-dioxa-4-aza-tricyclo[30.3.1.04,9]hexatriaconta-16,24,26,28-tetraene-2,3,10,14,20-pentaone) and described by the following structure:

The present invention further relates to the above pharmaceutical combination(s) for use in the treatment of a cancer.

The present invention further relates to a method for the treatment of a cancer comprising administering the above pharmaceutical combination(s) in jointly therapeutically effective amount, to a warm-blooded animal, preferably a human, in need thereof.

In accordance with the present invention, the compounds in the pharmaceutical combination(s) may be administered either as a single pharmaceutical composition, as separate compositions, or sequentially.

The present invention further relates to a kit comprising the pharmaceutical combination.

DETAILED DESCRIPTION OF THE FIGURES

DETAILED DESCRIPTION OF THE INVENTION

The following general definitions are provided to better understand the invention:

"Combination" refers to either a fixed combination in one dosage unit form, or a non-fixed combination (or kit of parts) for the combined administration where a compound and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The term "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "fixed combination" means that the active ingredients, e.g. a compound of formula A and a combination partner, are both administered to a patient simultaneously in the form of a single entity or dosage. The terms "non-fixed combination" or "kit of parts" mean that the active ingredients, e.g. a compound of formula A and a combination partner, are both administered to a patient as separate entities either simultaneously, concurrently or sequentially with no specific time limits, wherein such administration provides therapeutically effective levels of the two compounds in the body of the patient.

"Treatment" includes prophylactic and therapeutic treatment (including but not limited to palliative, curing, symptom-alleviating, symptom-reducing) as well as the delay of progression of a cancer disease or disorder. The term "prophylactic" means the prevention of the onset or recurrence of a cancer. The term "delay of progression" as used herein means administration of the combination to patients being in a pre-stage or in an early phase of the cancer to be treated, a pre-form of the corresponding cancer is diagnosed and/or in a patient diagnosed with a condition under which it is likely that a corresponding cancer will develop.

"Pharmaceutical preparation" or "pharmaceutical composition" refers to a mixture or solution containing at least one therapeutic agent to be administered to a warm-blooded, e.g., a human.

"Co-administer", "co-administration" or "combined administration" or the like are meant to encompass administration of the selected therapeutic agents to a single patient, and are intended to include treatment regimens in which the agents are not necessarily administered by the same route of administration or at the same time.

"Pharmaceutically acceptable" refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

"Therapeutically effective" preferably relates to an amount of a therapeutic agent that is therapeutically or in a broader sense also prophylactically effective against the progression of a cancer.

"Jointly therapeutically effective" means that the therapeutic agents may be given separately (in a chronologically staggered manner, especially a sequence-specific manner) in such time intervals that they prefer, in the warm-blooded animal, especially human, to be treated, still show a (preferably synergistic) interaction. Whether this is the case can, inter alia, be determined by following the blood levels, showing that both compounds are present in the blood of the human to be treated at least during certain time intervals.

"Single pharmaceutical composition" refers to a single carrier or vehicle formulated to deliver effective amounts of both therapeutic agents to a patient. The single vehicle is designed to deliver an effective amount of each of the agents, along with any pharmaceutically acceptable carriers or excipients. In some embodiments, the vehicle is a tablet, capsule, pill, or a patch. In other embodiments, the vehicle is a solution or a suspension.

"Dose range" refers to an upper and a lower limit of an acceptable variation of the amount of therapeutic agent specified. Typically, a dose of the agent in any amount within the specified range can be administered to patients undergoing treatment.

"Subject", "patient", or "warm-blooded animal" is intended to include animals. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from a brain tumor disease. Particularly preferred, the subject or warm-blooded animal is human.

The terms "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

The present invention relates to a pharmaceutical combination comprising (1) a CDK inhibitor or a pharmaceutically acceptable salt thereof and (2) a mTOR inhibitor or a pharmaceutically acceptable salt thereof.

Such combination may be for simultaneous, separate or sequential use for the treatment of a cancer.

In one embodiment, the CDK inhibitor is CDK4/6 inhibitor.

The CDK4/6 inhibitor can be, for example,

Compound A, described by Formula A below:

(A)

or pharmaceutically acceptable salt(s) thereof.

The mTOR inhibitor, in one embodiment, is everolimus (hereinafter referred as Compound B) which has the chemical name ((1R,9S,12S,15R,16E,18R,19R,21R,23S,24E,26E, 28E,30S,32S,35R)-1,18-dihydroxy-12-{(1R)-2-[(1S,3R, 4R)-4-(2-hydroxyethoxy)-3-methoxycyclohexyl]-1-methylethyl}-19,30-dimethoxy-15,17,21,23,29,35-hexamethyl-11, 36-dioxa-4-aza-tricyclo[30.3.1.04,9]hexatriaconta-16,24, 26,28-tetraene-2,3,10,14,20-pentaone) and described by the following structure:

The present invention further relates to the above pharmaceutical combination(s) for use in the treatment of a cancer.

The present invention further relates to a method for the treatment of a cancer comprising administering the above pharmaceutical combination(s) in jointly therapeutically effective amount, to a warm-blooded animal, preferably a human, in need thereof.

In accordance with the present invention, the compounds in the pharmaceutical combination(s) may be administered either as a single pharmaceutical composition, as separate compositions, or sequentially.

The present invention further relates to a kit comprising the pharmaceutical combination.

The Compounds A and B can be synthesized by one skilled in the art. Specifically, Compound A is disclosed as Example 74 of WO2010/020675.

Comprised are likewise the pharmaceutically acceptable salts thereof, the corresponding racemates, diastereoisomers, enantiomers, tautomers, as well as the corresponding crystal modifications of above disclosed compounds where present, e.g. solvates, hydrates and polymorphs, which are disclosed therein. The compounds used as active ingredients in the combinations of the present invention can be prepared and administered as described in the cited documents, respectively. Also within the scope of this invention is the combination of more than two separate active ingredients as set forth above, i.e., a pharmaceutical combination within the scope of this invention could include three active ingredients or more.

It is believed that the combination(s) of the present invention possesses beneficial therapeutic properties, e.g. synergistic interaction, strong in vitro or in vivo anti-proliferative activity and/or strong in vitro or in vivo antitumor response, which render it particularly useful for the treatment of cancer.

Suitable cancers that can be treated with the combination of the present invention include, but are not limited to, sarcoma, lymphomas, cancer of the lung, bronchus, prostate, breast (including sporadic breast cancers and sufferers of Cowden disease), pancreas, gastrointestine, colon, rectum, colon, colorectal adenoma, thyroid, liver, intrahepatic bile duct, hepatocellular, adrenal gland, stomach, gastric, glioma, glioblastoma, endometrial, melanoma, kidney, renal pelvis, urinary bladder, uterine corpus, cervix, vagina, ovary, multiple myeloma, esophagus, a leukaemia, acute myelogenous leukemia, chronic myelogenous leukemia, lymphocytic leukemia, myeloid leukemia, brain, a carcinoma of the brain, oral cavity and pharynx, larynx, small intestine, non-Hodgkin lymphoma, melanoma, villous colon adenoma, a neoplasia, a neoplasia of epithelial character, a mammary carcinoma, basal cell carcinoma, squamous cell carcinoma, actinic keratosis, tumor diseases (including solid tumors), a tumor of the neck or head, polycythemia vera, essential thrombocythemia, myelofibrosis with myeloid metaplasia, and Waldenstroem disease. Where a cancer, a tumor, a tumor disease, sarcoma, or a cancer are mentioned, also metastasis in the original organ or tissue and/or in any other location are implied alternatively or in addition, whatever the location of the tumor and/or metastasis.

In a particular embodiment, the cancer is breast cancer. In particular, the cancer is a breast cancer having either hormone receptor positive, a mutation in the PIK3CA, or a combination thereof. More specifically, the cancer is estrogen receptor positive (+) breast cancer.

In a further embodiment, the cancer is a hormone receptor positive (+) breast cancer resistant to treatment with hormone therapy (e.g., estrogen or progesterone). A cancer "resistant to treatment with hormone therapy" refers to a cancer or tumor that either fails to respond favorably to treatment with prior hormone therapy, or alternatively, recurs or relapses after responding favorably to hormone therapy. The cancer or tumor may be resistant or refractory at the beginning of treatment or it may become resistant or refractory during treatment.

In another embodiment, the cancer is rhabdoid tumor, particularly malignant rhabdoid tumor.

It is one objective of this invention to provide a pharmaceutical composition comprising a quantity, which is jointly therapeutically effective at targeting or preventing a cancer, of each therapeutic agent of the invention.

In accordance with the present invention, agents in the composition of the present invention may be administered together in a single pharmaceutical composition, separately in two or more separate unit dosage forms, or sequentially. The unit dosage form may also be a fixed combination.

The pharmaceutical compositions for separate administration of agents or for the administration in a fixed combination (i.e., a single galenical composition comprising at least two therapeutic agents according to the invention may be prepared in a manner known per se and are those suitable for enteral, such as oral or rectal, topical, and parenteral administration to subjects, including mammals (warm-blooded animals) such as humans, comprising a therapeutically effective amount of at least one pharmacologically active combination partner alone, e.g., as indicated above, or in combination with one or more pharmaceutically acceptable carriers or diluents, especially suitable for enteral or parenteral application. Suitable pharmaceutical compositions contain, e.g., from about 0.1% to about 99.9%, preferably from about 1% to about 60%, of the active ingredient(s).

Pharmaceutical compositions for the combination therapy for enteral or parenteral administration are, e.g., those in unit dosage forms, such as sugar-coated tablets, tablets, capsules or suppositories, ampoules, injectable solutions or injectable suspensions. Topical administration is e.g. to the skin or the eye, e.g. in the form of lotions, gels, ointments or creams, or in a nasal or a suppository form. If not indicated otherwise, these are prepared in a manner known per se, e.g., by means of conventional mixing, granulating, sugar-coating, dissolving or lyophilizing processes. It will be appreciated that the unit content of each agent contained in an individual dose of each dosage form need not in itself constitute an effective amount since the necessary effective amount can be reached by administration of a plurality of dosage units.

Pharmaceutical compositions may comprise one or more pharmaceutical acceptable carriers or diluents and may be manufactured in conventional manner by mixing one or both combination partners with a pharmaceutically acceptable carrier or diluent. Examples of pharmaceutically acceptable diluents include, but are not limited to, lactose, dextrose, mannitol, and/or glycerol, and/or lubricants and/or polyethylene glycol. Examples of pharmaceutically acceptable binders include, but are not limited to, magnesium aluminum silicate, starches, such as corn, wheat or rice starch, gelatin, methylcellulose, sodium carboxymethylcellulose and/or polyvinylpyrrolidone, and, if desired, pharmaceutically acceptable disintegrators include, but are not limited to, starches, agar, alginic acid or a salt thereof, such as sodium alginate, and/or effervescent mixtures, or adsorbents, dyes, flavorings and sweeteners. It is also possible to use the compounds of the present invention in the form of parenterally administrable compositions or in the form of infusion solutions. The pharmaceutical compositions may be sterilized and/or may comprise excipients, for example preservatives, stabilizers, wetting compounds and/or emulsifiers, solubilisers, salts for regulating the osmotic pressure and/or buffers.

In particular, a therapeutically effective amount of each of the combination partner of the combination of the invention may be administered simultaneously or sequentially and in any order, and the components may be administered separately or as a fixed combination. For example, the method of preventing or treating a cancer according to the invention may comprise: (i) administration of the first agent in free or pharmaceutically acceptable salt form; and (ii) administration of a second agent in free or pharmaceutically acceptable salt form, simultaneously or sequentially in any order, in jointly therapeutically effective amounts, preferably in synergistically effective amounts, e.g., in daily or intermittently dosages corresponding to the amounts described herein. The individual combination partners of the combination of the invention may be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each of combination partner agents employed in the combination of the invention may vary depending on the particular compound or pharmaceutical composition employed, the mode of administration, the condition being treated, the severity of the condition being treated. Thus, the dosage regimen of the combination of the invention is selected in accordance with a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy requires a regimen based on the kinetics of the drug's availability to target sites. This involves a consideration of the distribution, equilibrium, and elimination of a drug.

A further benefit is that lower doses of the active ingredients of the combination of the invention can be used, e.g., that the dosages need not only often be smaller but are also applied less frequently, or can be used in order to diminish the incidence of side effects. This is in accordance with the desires and requirements of the patients to be treated.

The combination of the agents can be combined in the same pharmaceutical preparation or in the form of combined preparations "kit of parts" in the sense that the combination partners can be dosed independently or by use of different fixed combinations with distinguished amounts of the combination partners, i.e., simultaneously or at different time points. The parts of the kit of parts can then, e.g., be administered simultaneously or chronologically staggered, that is at different time points and with equal or different time intervals for any part of the kit of parts.

The present invention further relates to a kit comprising a first compound that is Compound A or pharmaceutically acceptable salts thereof, a second compound that is Compound B or pharmaceutically acceptable salts thereof, and a package insert or other labeling including directions for treating a cancer.

The following Examples illustrate the invention described above; they are not, however, intended to limit the scope of the invention in any way. The beneficial effects of the pharmaceutical combination of the present invention can also be determined by other test models known as such to the person skilled in the pertinent art.

Example 1

The following experimental procedure is performed to demonstrate the efficacy and anti-proliferative activity of Compound A and Compound B in combination in the treatment of ER+ breast cancer or rhabdoid tumor.

T-47D and MCF-7 are two ER+ breast cancer cell lines.

A204 and G401T-47D are two rhabdoid tumor cell lines.

Shown are surface plots of growth inhibitory effects (inhibition) and synergy measurements (ADD excess/Loewe excess) for combinations between Compound A and Compound B. In the "inhibition" plots leftmost columns and bottom rows show growth inhibition by Compound A and Compound B, as single agents respectively. Combinations of the two compounds are in matrix format, with each point in the grid containing the concentration of the single agents given on the corresponding point on the X and Y axis. The percentage of growth inhibition achieved for each point is given numerically within the small boxes, and depicted graphically with colors. In the "excess" plots, excess inhibition of growth at each combination point is shown numerically and graphically with larger numbers and lighter colors indicating greater synergistic activity. Numbers at or near 0 represent additivity and numbers below 0 represent regions of antagonism. All calculations and graphical depictions have been previously described in Lehar et al. (Lehar J, Krueger A S, Avery W, et al (2009) Synergistic drug combinations tend to improve therapeutically relevant selectivity. Nat Biotechnol 27, 659-66.).

The results from Example 1 are shown in FIGS. 1-4. Synergy scores for this combination indicate that in all cases co-treatment of Compound A and Compound B led to synergistic growth inhibition.

Example 2

MCF-7 cells were purchased from American Type Culture Collection (ATCC). They were tested free of mycoplasma and viral contamination in the IMPACT VIII PCR assay panel (RADIL, MU Research Animal Diagnostic Laboratory, Columbia, Mo.). They were cultured in EMEM medium (ATCC#30-2003) containing 10% heat inactivated fetal bovine serum, and were at passage 18 for this experiment. Female, nude mice from Harlan (Hsd:Athymic Nude-Foxn1nu) were used in this xenograft study. Mice received 17b-estradiol pellets (0.18 mg/pellet, 90-day release) (Innovative research of America Catalog # NE-121) implanted between the shoulder blades three days before cell implantation. Tumor volume and body weight were monitored throughout the experiment.

In this MCF7 experiment, Compound A monotherapy at 75 mg/kg yielded T/T0 of −9%. Compound B monotherapy at 5 mg/kg achieved T/T0 of −21%. The combination of Compound A and Compound B achieved T/T0 of −49%. Mean body weight loss was less than 8% in all the aforementioned groups. The results indicate that the combination of Compound A and Compound B exhibit additional benefit over either monotherapy against the ER+, PIK3CA mutant breast tumor model, MCF7, in vivo. The data support the testing of Compound A and Compound B in the relevant clinical setting.

Figure 1:
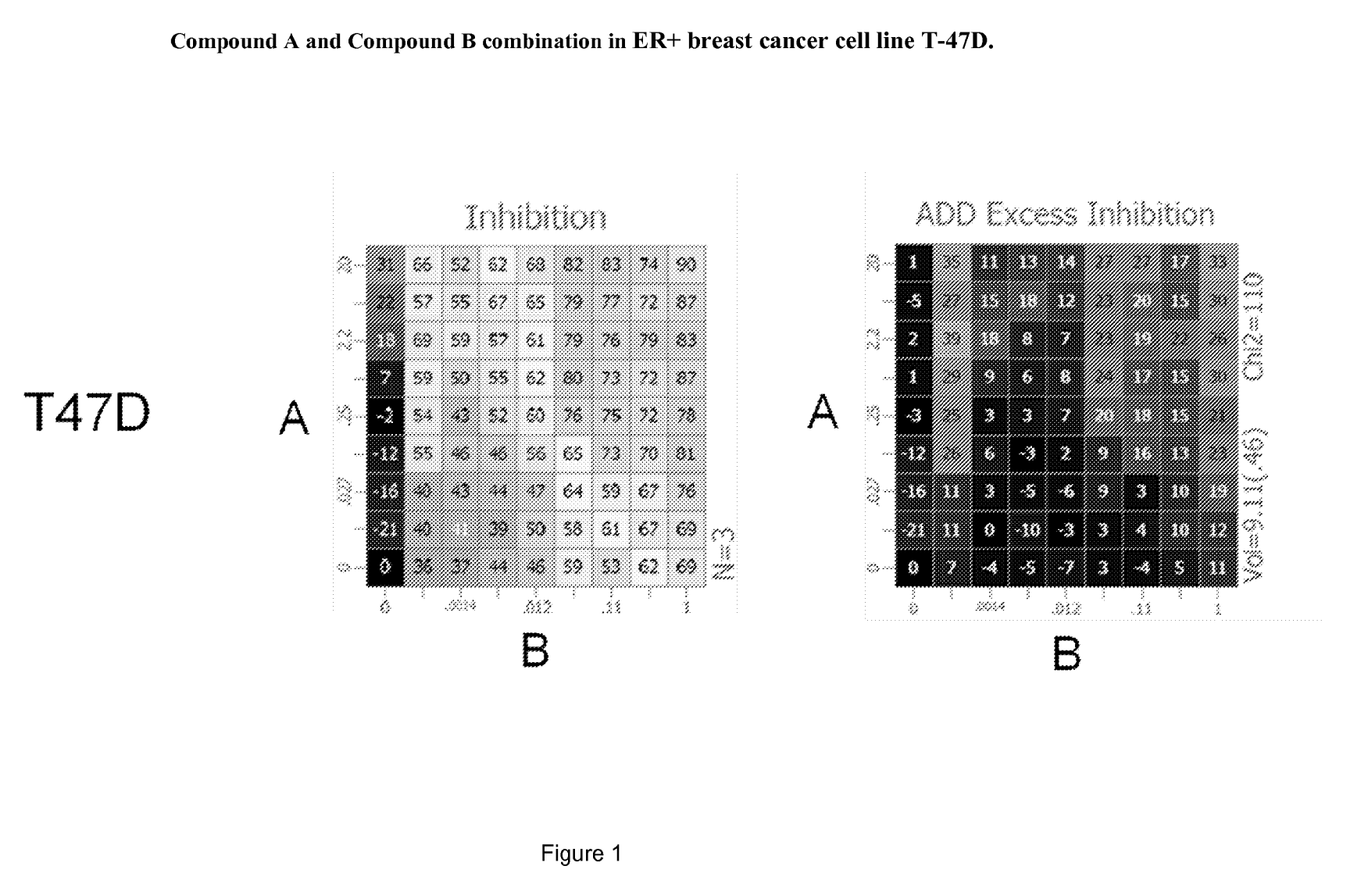
FIGS. 1-4 show combination studies in two ER+ breast cancer cell lines, T-47D and MCF-7, and two rhabdoid tumor cell lines A204 and G401. Synergy scores for this combination indicate that in all cases co-treatment of Compound A and Compound B led to synergistic growth inhibition.
Figure 2:
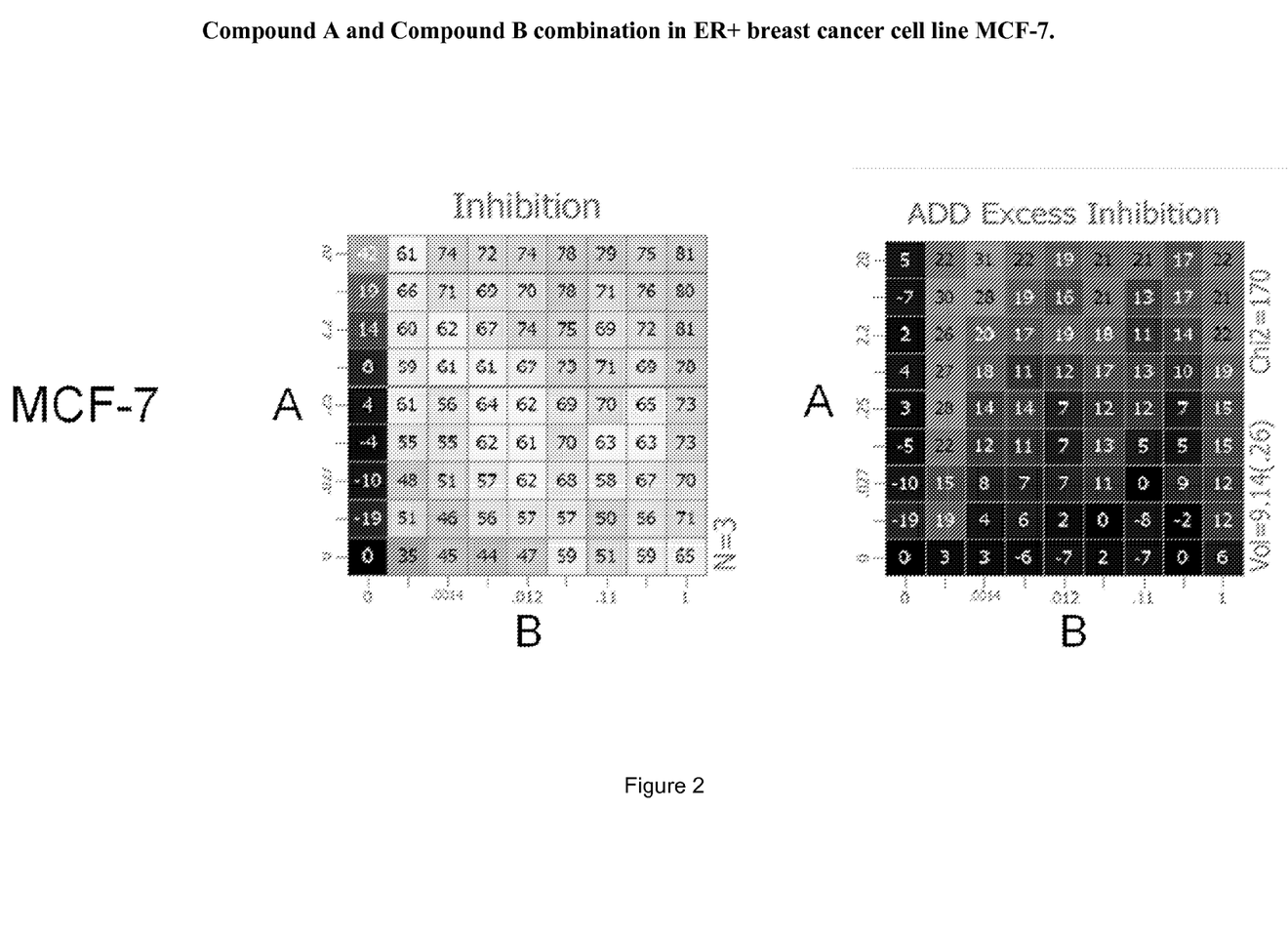
Figure 3:
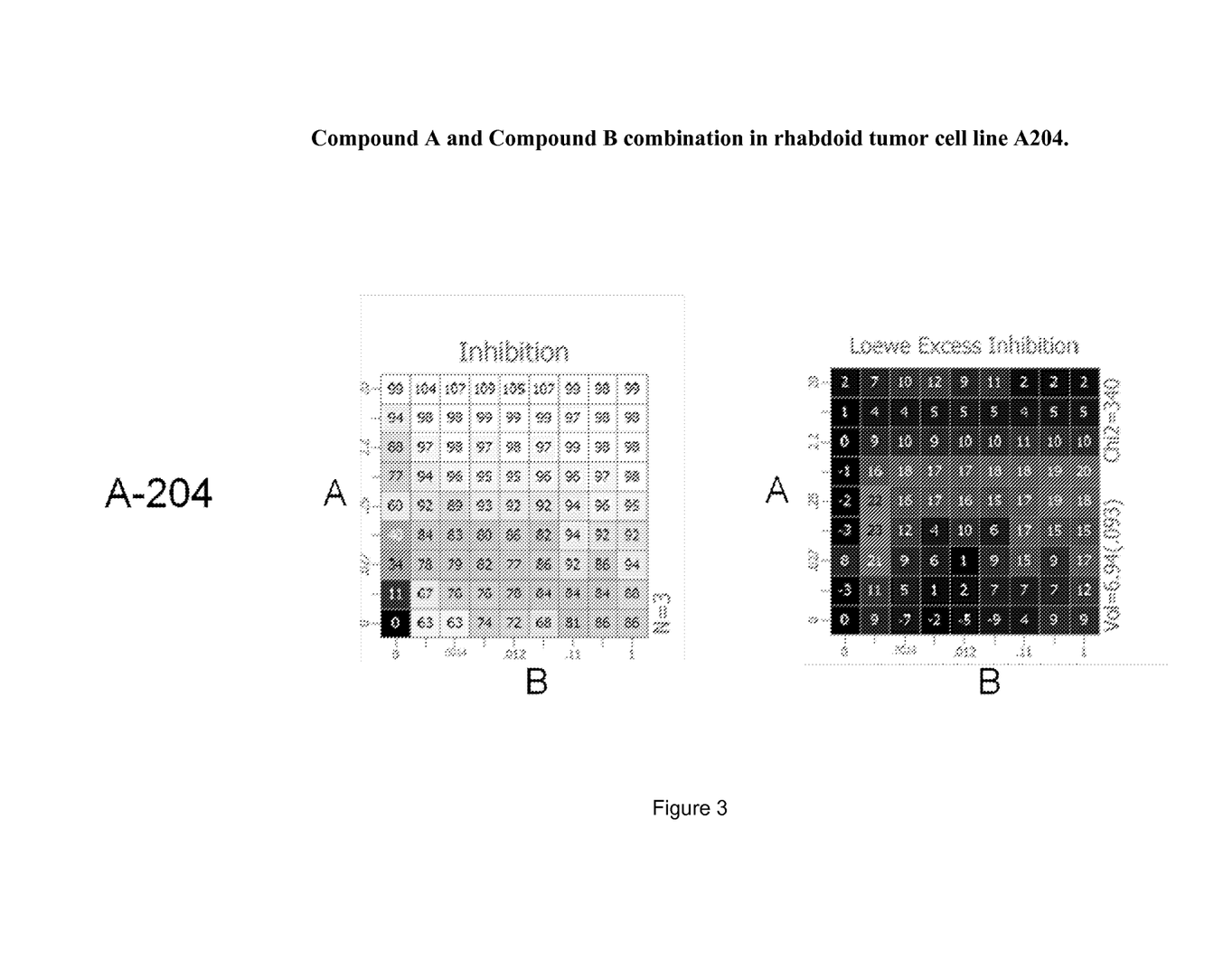
Figure 4:
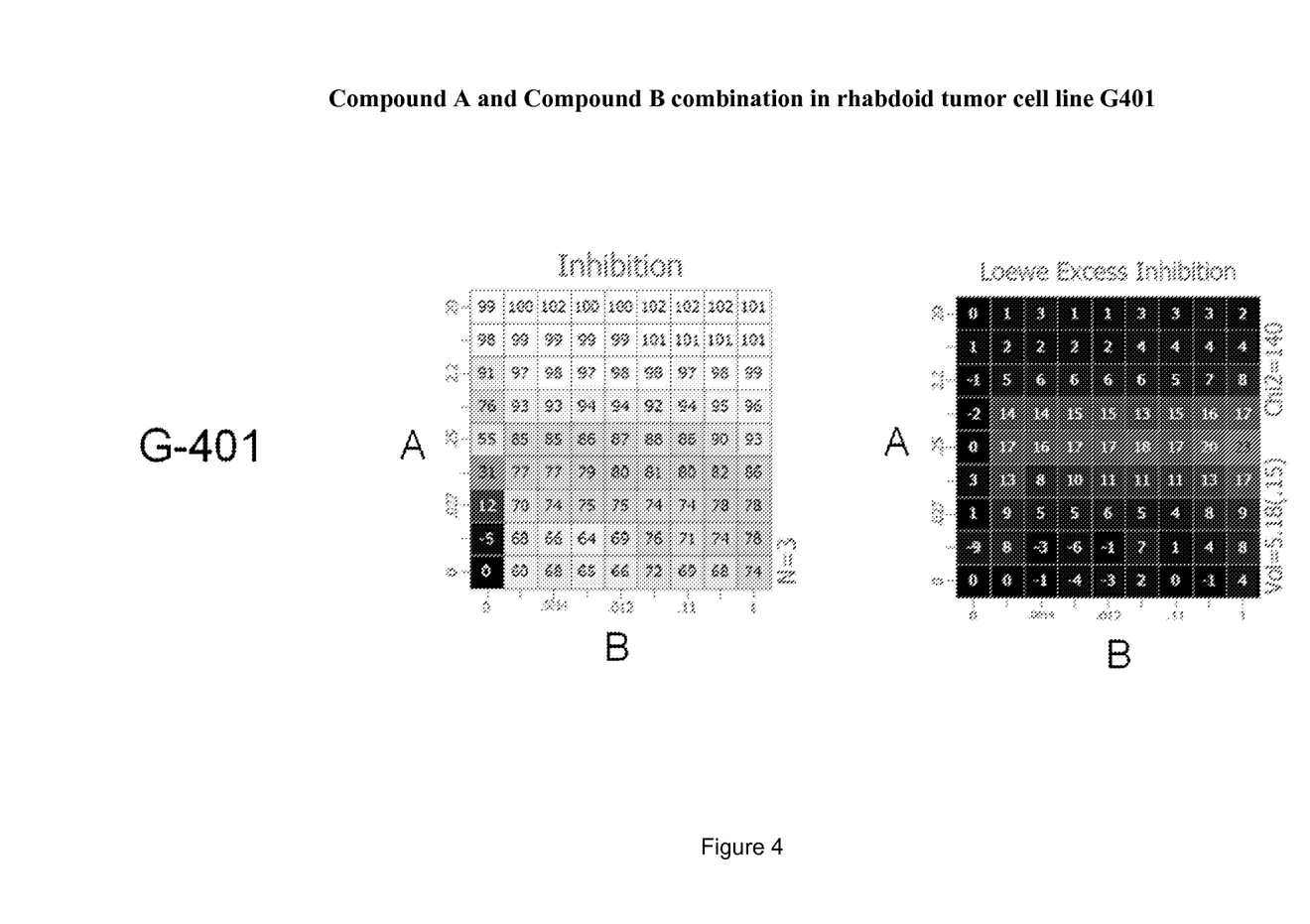
Figure 5:
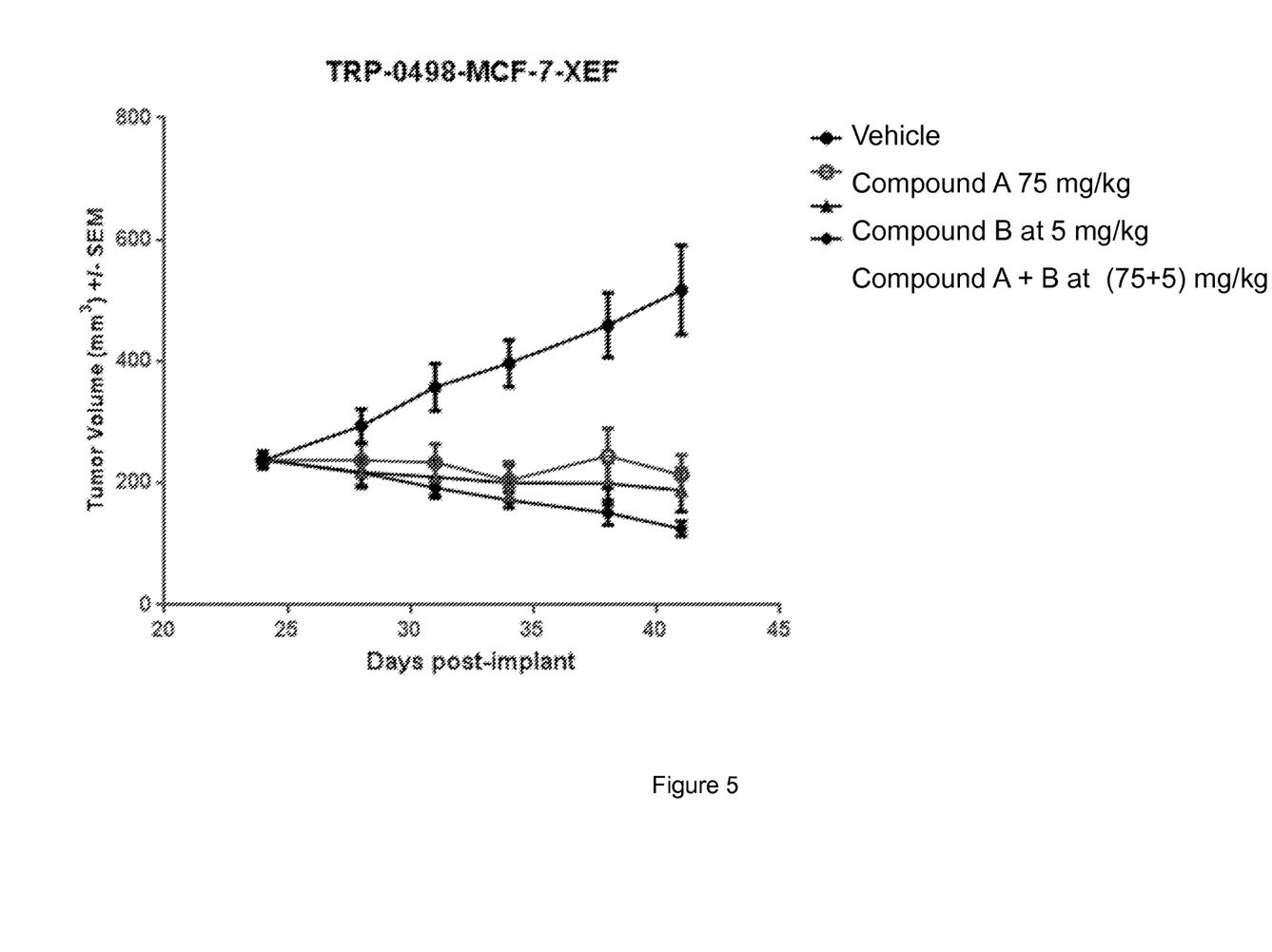
FIG. 5 shows the effect of Compound A and Compound B combination in MCF7 tumor xenograft model in vivo.

The results from Example 2 are shown in FIG. 5.

The invention claimed is:

1. A method of treating ER+ breast cancer comprising administering to a subject in need of such treatment a combination comprising a first agent that is a cyclin dependent kinase 4 or cyclin dependent kinase 6 (CDK4/6) inhibitor and a second agent that is an mTOR inhibitor.

2. The method of claim 1, wherein the agents are administered simultaneously, separately or sequentially.

3. The method of claim 1, wherein the CDK inhibitor is CDK4/6 inhibitor.

4. The method of claim 3, wherein the CDK4/6 inhibitor is Compound A, described by Formula A below:

(A)

or pharmaceutically acceptable salt thereof.

5. The method of claim 1, wherein the mTOR inhibitor is everolimus.

6. A method of treating malignant rhabdoid tumor comprising administering to a subject in need of such treatment a combination comprising a first agent that is a cyclin dependent kinase 4 or cyclin dependent kinase 6 (CDK4/6) inhibitor and a second agent that is an mTOR inhibitor.

7. The method of claim 6, wherein the agents are administered simultaneously, separately or sequentially.

8. The method of claim 6, wherein the CDK inhibitor is CDK4/6 inhibitor.

9. The method of claim 8, wherein the CDK4/6 inhibitor is Compound A, described by Formula A below:

(A)

or pharmaceutically acceptable salt thereof.

10. The method of claim 6, wherein the mTOR inhibitor is everolimus.

* * * * *